United States Patent [19]

Lewis et al.

[11] Patent Number: 5,314,679
[45] Date of Patent: May 24, 1994

[54] VASCULAR MAGNETIC RESONANCE IMAGING AGENT COMPRISING NANOPARTICLES

[75] Inventors: Jerome M. Lewis, Newton; Edward T. Menz, Quincy; Francis E. Kenny, Watertown; Ernest V. Groman, Brookline; Lee Josephson, Arlington, all of Mass.

[73] Assignee: Advanced Magnetics Inc., Cambridge, Mass.

[21] Appl. No.: 995,111

[22] Filed: Dec. 22, 1992

Related U.S. Application Data

[60] Continuation of Ser. No. 769,310, Oct. 1, 1991, abandoned, which is a division of Ser. No. 233,177, Aug. 16, 1988, Pat. No. 5,055,288, which is a continuation-in-part of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.$^5$ .................. A61B 5/055; A61K 33/26; A61K 37/14; A61K 31/715
[52] U.S. Cl. .................. 424/9; 424/646; 424/648; 514/6; 514/54; 514/60; 128/653.4; 436/173; 436/806
[58] Field of Search .................. 424/9, 646, 648; 436/173, 806; 128/653.4, 654, 653.1; 514/54, 60, 6

[56] References Cited

U.S. PATENT DOCUMENTS

| | | | |
|---|---|---|---|
| 3,697,502 | 10/1975 | Christensen | 536/113 |
| 3,980,076 | 9/1976 | Wikswo, Jr. et al. | 128/653.1 |
| 4,101,435 | 7/1978 | Hasegawa et al. | 536/113 |
| 4,599,405 | 7/1986 | Muller et al. | 536/113 |
| 4,675,173 | 6/1987 | Widder | 424/9 |
| 4,695,392 | 9/1987 | Whitehead et al. | 262/62.54 |
| 4,731,239 | 3/1988 | Gordon | 424/9 |
| 4,735,796 | 4/1988 | Gordon | 536/113 |
| 4,827,945 | 5/1989 | Groman et al. | 128/653 |
| 4,951,675 | 8/1990 | Groman et al. | 128/653.4 |
| 5,114,703 | 5/1992 | Wolf et al. | 424/5 |

FOREIGN PATENT DOCUMENTS

| | | |
|---|---|---|
| 571966 | 10/1988 | Belgium . |
| 625770 | 8/1961 | Canada . |
| 0186616 | 9/1990 | European Pat. Off. . |
| 1196629 | 7/1965 | Fed. Rep. of Germany . |
| 1954960 | 5/1970 | Fed. Rep. of Germany . |
| 3443251A | 11/1984 | Fed. Rep. of Germany . |
| 1200702 | 8/1970 | United Kingdom . |
| WO83/03920 | 11/1983 | World Int. Prop. O. . |
| WO85/02772 | 7/1985 | World Int. Prop. O. . |
| WO85/04330 | 10/1985 | World Int. Prop. O. . |
| WO86/01112 | 2/1986 | World Int. Prop. O. . |

OTHER PUBLICATIONS

Widder, D. J.; Greif, W. L.; Widder, K. J.; Edelman, R. R.; Brady, T. J. "Magnetite Albumin Microspheres: A
(List continued on next page.)

Primary Examiner—Gary E. Hollinden
Attorney, Agent, or Firm—Pennie & Edmonds

[57] ABSTRACT

The preparation and isolation of biodegradable superparamagnetic MR imaging contrast agents for the vascular compartment is described. These aggregates are comprised of individual biodegradable superparamagnetic metal oxide crystals which aggregates have an overall mean diameter less than about 4000 angstroms. The preferred vascular imaging contrast agent is comprised of aggregates of iron oxide crystals having an overall mean diameter less than about 500 angstroms. These contrast agents may be associated with a macromolecular species, which assist, among other things, in the preparation of these extremely small materials, and may be dispersed or dissolved in a physiologically acceptable medium. Preferred media also stabilize the materials against further aggregation even under harsh sterilization conditions. The autoclaved biodegradable superparamagnetic iron oxides of the invention are ideally suited for a pharmaceutical preparation and enjoy several advantages over prior intravascular imaging contrast media including low osmolality, low effective dose requirements, high relaxivities, long blood lifetimes, rapid biodegradability, and versatility with respect to a wide range of applicable MR data acquisition parameters.

42 Claims, 4 Drawing Sheets

OTHER PUBLICATIONS

New MR Contrast Material," *Amer. J. Roentgenology* 1987, 148, 399.

Olsson, M. B. E.; Persson, B. R. R.; Salford, L. G.; Schroeder, U. "Super-Paramagnetic Particles as $T_2$ Contrast Agent in Photon MR-Imaging," *Magnetic Resonance Imaging* 1986, 4(2), 142.

Ohgushi, M.; Nagayama, K.; Wada, A. "Dextran-Magnetite: A New Relaxation Reagent and Its Application to $T_2$ Measurements in Gel Systems," *J. Magnetic Resonance* 1978, 29, 599.

Renshaw, P. F.; Owen, C. S.; McLaughlin, A. C.; Frey, T. G.; Leigh, Jr, J. S. "Ferromagnetic Contrast Agents: A New Approach," *Magnetic Resonance in Medicine* 1986, 3, 217.

Dias, M. H. M.; Lauterbur, P. C. "Ferromagnetic Particles as Contrast Agents for Magnetic Resonance Imaging of Liver and Spleen," *Magnetic Resonance in Medicine* 1986, 3 328.

Hemmingsson, A.; Carlsten, J.; Ericsson, A.; Klaveness, J.; Sperber, G. O.; Thuomas, K. A. "Relaxation Enhancement of the Dog Liver and Spleen by Biodegradable Superparamagnetic Particles in Proton Magnetic Resonance Imaging," *Acta Radiologica* 1987, 28(6) 703.

Kent, T. A.; Quast, M. J.; Kaplan B. J.; Amparo E. G.; Gevedon, R. M.; Garza, E.; Salina, F.; Ward, G.; Suttle, A. D.; Eisenberg, H. M. "Cerebral Blood Flow Mapping Using Magnetite Microspheres," *Book of Abstracts, Society of Magnetic Resonance in Medicine, Sixth Annual Meeting and Exhibition,* 1987, p. 5.

Bacon, B. R.; Stark, D. D.; Park. C. H.; Saini, S.; Groman, E. V.; Hahn, P. F.; Compton, C. C.; Ferrucci, J. T. "Ferrite Particles: A New Magnetic Resonance Imaging Agent, Lack of Acute or Chronic Hepatotoxicity After Intravenous Administration," *J. Lab. Clin. Med.* 1987, 110(2), 164.

Saini, S.; Stark, D. D.; Hahn, P. F.; Wittenberg, J.; Brady T. J.; Ferrucci, Jr., J. T. "Ferrite Particles: A Superparamagnetic MR Contrast Agent for the Reticuloendotheial System," *Radiology* 1987, 162, 211.

Hahn, P. F.; Stark, D. D.; Saini, S.; Lewis, J. M.; Wittenberg, J.; Ferrucci, J. T. "Ferrite Particles for Bowel Contrast in MR Imaging: Design Issues and Feasability Studies," *Radiology* 1987, 164, 37.

Sani, S.; Stark, D. D.; Hahn, P. F.; Bousquet, J. C.; Introcasso, J.; Wittenberg, J.; Brady, T. J.; Ferrucci, J. T. "Ferrite Particles: A Superparamagnetic MR Contrast Agent for Enhanced Detection of Liver Carcinoma," *Radiology* 1987, 162, 217.

Weissleder, R.; Hahn, P. F.; Stark, D. D.; Rummeny, E.; Saini, S.; Wittenberg, J.; Ferrucci, J. T. "MR Imaging of Splenic Metastases: Ferrite-Enhanced Detection in Rats," *Am. J. Roetngenology* 1987, 149, 723.

Weissleder, R.; Saini, S.; Stark, D. D.; Elizondo, G.; Compton, C.; Wittenberg, J.; Ferrucci, Jr., J. T. "Pyogenic Liver Abscess: Contrast-Enhanced MR Imaging in Rats," *Am. J. Roentgenology* 1988 150, 115.

Weissleder, R.; Saini, S.; Stark, D. D.; Wittenberg, J.; Ferrucci, J. T. "Dual-Contrast MR Imaging of Liver Cancer in Rats," *Am. J. Roentgenology* 1988, 150, 561.

Weissleder, R.; Stark, D. D.; Compton, C. C.; Wittenberg, J.; Ferrucci, J. T. "Ferrite-Enhanced MR Imaging of Hepatic Lymphoma: An Experimental Study in Rats," *Am. J. Roentgenology* 1987, 149, 1161.

Weissleder, R.; Stark, D. D.; Rummeny, E. J.; Compton, C. C.; Ferrucci, J. T. "Splenic Lymphoma: Ferrite-Enhanced MR Imaging in Rats," *Radiology* 1988, 166, 423.

Tsang, Y. M.; Stark, D. D.; Chen, M. C. M.; Weissleder, R.; Wittenberg, J.; Ferrucci, J. T. "Hepatic Micrometastases in the Rat: Ferrite-Enhanced MR Imaging," *Radiology,* 1988, 167, 21.

Dean, P. B.; Paajanen, H. "Undesirable Consequences of Intravascular Contrast Media Administration," in *Contrast Media Biological Effects and Clinical Application,* vol. 1, pp. 69–75 (Parvez, Z. ed. 1987).

Schmiedel, U.; Ogan, M.; Paajanen, H.; Marotti, M.; Crooks, L. E.; Brito, A. C.; Brasch, R. C. "Albumin Labeled with Gd-DTPA as an Intravascular, Blood Pool-Enhancing Agent for MR Imaging: Biodistribution and Imaging Studies," *Radiology* 1987, 162, 205.

Meleon, C. E.; Pomerantz, Y. "Carbohydrates," in *Food Analysis Laboratory Experiments,* ch. 26, 1973.

Davis, P. L.; et al. "Interactions of Paramagnetic Contrast Agents and the Spin Echo Pulse Sequence," *Investigative Radiology* 23:381–387 (1988).

Saini, S., et al. "Advances in Contrast-Enhanced MR Imaging," *AJR* 156:235–239 (1991).

(List continued on next page.)

OTHER PUBLICATIONS

Hahn, P. F., "Gastrointestinal Contrast Agents," *AJR* 156:252–254 (1991).

Massart, R. "Preparation of Aqueous Magnetic Liquids in Alkaline and Acidic Media," *IEEE Transactions on Magnetics* 17(2):1247–1248 (1991).

Federico, M., et al., "Tissue Distribution of Dextran Magnetite in the Rat Studied by ESR Spectroscopy," *Book of Abstracts, vol. 2, Society of Magnetic Resonance in Medicine, Eighth Annual Meeting and Exhibition*, p. 794 (1989).

Pouliquen, D., et al. "Superparamagnetic Iron Oxide Nanoparticles as a Liver MRI Contrast Agent: Contribution of Microencapsulation to Improved Biodistribution," *Magnetic Resonance Imaging* 7:619–627 (1989).

Widder, D. J., et al. "Magnetic Albumin Microspheres: A New MR Contrast Material," *AJR* 148:399–404 (1987).

Josephson, L., et al. "A Functionalized Superparamagnetic Iron Oxide Colloid as a Receptor Directed MR Contrast Agent," *Magnetic Resonance Imaging* 8:637–646 (1990).

Weissleder, R., et al. "Ultrasmall Superparamagnetic Iron Oxide: Characterization of New Class of Contrast Agents for MR Imaging," *Radiology* 175:489–493 (1990).

Illum, L., et al. "Surface Characteristics and the Interaction of Colloidal Particles with Mouse Peritoneal Macrophages," *Biomaterials* 8:113–117 (1987).

Kawaguchi, H. et al., "Phagocytosis of latex particles by leucocytes. I. Dependence of phagocytosis on the size and surface potential of particles," *Biomaterials* 7:61–66 (1986).

Jones, E. A., et al. "Kupffer Cells," *The Liver: Biology and Pathobiology, Second Edition*, Ch. 37, pp. 683–688 (Arias, IM., et al. eds. 1988).

VASCULAR MAGNETIC RESONANCE IMAGING AGENT COMPRISING NANOPARTICLES

CROSS REFERENCE TO RELATED APPLICATIONS

This is a continuation of U.S. application Ser. No. 07/769,310, filed Oct. 1, 1991, now abandoned which, in turn, is a division of U.S. application Ser. No. 07/233,177, filed Aug. 16, 1988, now U.S. Pat. No. 5,055,288, which, in turn, is a continuation-in-part of U.S. application Ser. No. 07/067,586, filed Jun. 26, 1987, now U.S. Pat. No. 4,827,945, which, in turn, is a continuation-in-part of U.S. application Ser. No. 06/882,044, filed Jul. 13, 1986, now U.S. Pat. No. 4,770,183, the disclosures of which are incorporated by reference herein in their entirety.

TABLE OF CONTENTS

1. Introduction
2. Background of the Invention
3. Definition
4. Summary of the Invention
5. Brief Description of the Figures
6. Detailed Description of the Invention
7. Examples
   7.1. Preparation of Sterilized Superparamagnetic Fluids
   7.2. Further Removal of Dextran from Sterilized Superparamagnetic Fluids
   7.3. Modified Procedure for the Preparation of Extremely Small Biodegradable Superparamagnetic Aggregates
   7.4. Gel Exclusion Chromatography of Superparamagnetic Materials
   7.5. Determination of Blood Lifetimes of Superparamagnetic Materials as a Function of Size
   7.6. Transmission Electron Microscopy Studies
   7.7. Superparamagnetic Fluids as Brightening Agents

1. INTRODUCTION

This invention relates to methods for enhancing magnetic resonance (MR) images of the vascular compartment of animal or human subjects. The methods of the present invention involve the use of biodegradable superparamagnetic contrast agents which enhance MR images of the vascular compartment. These methods, in turn, allow one to image organ or tissue perfusion, as well as blood flow. The use of these contrast agents, preferably administered as a superparamagnetic fluid, offers significant advantages over existing methodologies including inter alia high proton relaxivities, rapid biodegradability, control of blood lifetimes, versatility in choice of pulse sequence weighting schemes and other MR experimental parameters, low dosage requirements, low osmolality, and little or no toxicity.

2. BACKGROUND OF THE INVENTION

Magnetic resonance (MR) imaging is widely regarded as a powerful technique for probing, discovering, and diagnosing the presence and progress of a pathological condition or disease. The MR method of imaging is also regarded as the least invasive of the imaging techniques presently available and does not expose the patient or subject to potentially harmful high-energy radiation, such as X-rays, or radioactive isotopes, such as technetium-99m. Technological developments in both instrumentation and computer software continue to improve the availability and quality of the images produced. Researchers discovered quickly, however, that the relative differences between the chemical and magnetic environments of water molecules, whose proton nuclei provide by far the largest source of measurable signal intensity within the body, whether these molecules be located in organs, tissues, tumors, or in the vascular compartment, are often quite small and, consequently, the resulting images are poorly resolved. Fortunately, this inherent limitation can be overcome by the use of proton relaxation agents, also known as contrast agents, which are absorbed selectively by different types of tissues and/or sets of organs, and thus create a temporary condition in which the magnetic environments of neighboring water molecules are measurably dissimilar.

According to their magnetic properties, there are three general types of MR contrast agents: paramagnetic, ferromagnetic, and superparamagnetic. The weak magnetism of paramagnetic substances arises from the individual unpaired electrons while the stronger magnetism of ferromagnetic and superparamagnetic materials results from the coupling of unpaired electrons made possible by their presence in crystalline lattices. Ferromagnetic materials retain their magnetism in the absence of an applied magnetic field while superparamagnetic materials lose their magnetism when the applied magnetic field is removed. With respect to effects on proton relaxation, paramagnetic agents have been termed $T_1$ type agents because of their ability to enhance spin-lattice or longitudinal relaxation of proton nuclei. Ferromagnetic agents have been termed $T_2$ type agents because of their specific effects on $T_2$, sometimes called the spin-spin or transverse relaxation.

There are three major disadvantages to the use of paramagnetic chelates as vascular MR contrast agents. The first is that many low molecular weight, ionic materials which are commonly used as paramagnetic chelates are hypertonic. The use of hypertonic solutions often results in adverse reactions upon injection. The second disadvantage is that paramagnetic chelates have short blood lifetimes whereas a vascular MR contrast agent should remain confined to the vascular compartment for long periods of time. Third, removal of paramagnetic chelates from the vascular compartment can result in release of the paramagnetic ion from the chelate. Paramagnetic ions of iron, manganese, and gadolinium, for example, are toxic in their free ionic form. Vascular MR contrast agents should have a benign metabolic fate after removal from the vascular compartment. These three disadvantages are explained further below.

Paramagnetic materials that have been used as $T_1$ contrast agents generally include organic free radicals as well as transition metal salts and chelates. These compounds can be quite soluble and, in the case of most transition metal complexes, are highly charged, ionic species. Due to their relatively low relaxivities (their ability to increase the relaxation rates of protons as a function of dose), high concentrations of transition metal chelates are needed to effect useful alterations in the relaxation times of blood. In addition, the ionic nature of many transition metal ion salts and chelates contributes to the high osmotic pressure of the injected diagnostic solutions. The end result is that solutions of paramagnetic materials, whether they are used as MR agents or not, tend to be hyperosmotic relative to blood.

The administration of hyperosmotic solutions into the subject is widely believed to be a major cause of ad actions to radiographic and MR contrast media (See, McClennan, B. L. *Diagnostic Imaging Supplement* 1987, 16–18 (December); "Contrast Media: Biological Effects and Clinical Application," Vol. Ch, 5 I, Parvez, Z., Moncada, R., and Sovak, M. (Eds.), CRC Press, Boca Raton, Florida (1987)).

The usual approach to the development of MR contrast agents confined to the vascular compartment for long periods of time is to increase the molecular weight of paramagnetic chelates by attaching the chelates to high molecular weight polymers. After injection, high molecular weight forms of the chelates cannot be excreted by glomerular filtration, and consequently have longer residence times within the vascular compartment. High molecular weight forms of chelates can be made by covalently attaching chelators to macromolecules such as human serum albumin (Schmiedl et al. *Radiology* 1987, 162, 205–210)). With this approach to the design of vascular YR contrast agents, the fate of the gadolinium after degradation of the agent presents serious problems. The long term retention of gadolinium not eliminated by glomerular filtration, and the potential for delayed toxicity from that element, pose major obstacles to the administration of high molecular weight gadolinium chelates to humans.

A major disadvantage of present ferromagnetic contrast agents is that such materials are relatively large and, frankly particulate in character. Frankly particulate materials, those generally having overall dimensions between about 0.5–10 microns, are quickly removed from the blood by the phagocytic action of the cells of the reticuloendothelial system, limiting the duration of their effects on the spin-spin and spin-lattice relaxation times of blood. Hence their usefulness as vascular MR contrast agents is limited. All particulate agents suffer a similar limitation.

3. DEFINITIONS

Unless otherwise noted, the term "sterilized" describes a sample or a preparation which has been subjected to any method known in the art which completely destroys all bacteria and other infectious agents which may be present in the sample or preparation. Nonlimiting examples of such methods include autoclaving, ultraviolet or gamma irradiation, cold membrane filtration, or chemical treatment. The resulting preparation is then suitable for in vivo and/or clinical use with or without further treatment. The term "biodegradable" describes a property of a compound or complex which allows the compound or complex to be broken down into smaller innocuous components and be excreted from or utilized within the body. The term "polyfunctional" applies to a molecule which contains a plurality of identical functional groups. A "macromolecular species" may include any molecule, natural or synthetic, which has a molecular weight in excess of 1 kilodalton.

Abbreviations used in the text are defined below.
$T_1$ = spin-lattice relaxation time
$T_2$ = spin-spin relaxation time
EM = transmission electron microscopy
MR = magnetic resonance or nuclear magnetic resonance (NMR)
RES = reticuloendothelial system
MW = molecular weight
kD = kilodalton

4. SUMMARY OF THE INVENTION

This invention relates to a method for enhancing an MR image of the vascular compartment of an animal or human subject. The enhanced MR image is realized by administering to such an animal or human subject an effective amount of a contrast agent prepared from aggregates of individual biodegradable superparamagnetic metal oxide crystals. The aggregates, whose metal oxide crystals may be associated with a macromolecular species, are dispersed in a physiologically acceptable medium, preferably an aqueous citrate buffer, which stabilizes the aggregates of the resulting fluid against further aggregation even under the sometimes extreme conditions of sterilization. The preparation of biodegradable superparamagnetic aggregates are described whose properties and characteristics, such as overall sizes and blood circulation lifetimes, for example, may be varied.

One of the objects of the present invention is to provide a pharmaceutical preparation of a biodegradable superparamagnetic contrast agent suitable for human clinical use in magnetic resonance experiments. In particular, preferred embodiments of the invention have great utility in obtaining enhanced images of the vascular system, of the blood pool, or of organ or tissue perfusion. By practicing the methods of the invention, blood vessels, arteries, veins, capillaries, as well as lymph vessels may be imaged successfully. In particular capillary beds of various organs or tissues such as the brain, the kidney, the lung, and the heart can be visualized. Such methods can thus provide valuable information regarding the condition of these vessels, organs, or tissues including the presence of microocclusions, embolisms, aneurysm, restricted blood flow, and the onset or recession of arterial disease.

It is also an object of this invention to provide a contrast agent which can serve as a brightening or a darkening agent, or both, and which is effective at low doses. This invention also seeks to provide a contrast agent which is rapidly biodegraded, being either excreted from or utilized within the body of the subject, as evidenced by a return of the proton relaxation rates of afflicted tissue to pre-administration levels within about one week of the initial administration. Sterile solutions containing these contrast agents may be isotonic. Yet another object of the present invention is to provide sterile solutions of a contrast agent which have a low osmotic pressure, low enough, in fact, that added salt may be included in the formulation if so desired. Hypotonic solutions of contrast media may thus be prepared, if so desired. It is also an object of the present invention to provide a contrast agent whose blood lifetime may be adjusted to accommodate the variable needs of the MR imaging experiment.

It is thus an object of the instant invention to provide an effective contrast agent with all the advantages enumerated above yet is substantially free of the limitations and objectionable aspects associated with paramagnetic and ferromagnetic materials.

After a thorough consideration of the foregoing disclosures and those that follow, other objects of the present invention become readily apparent to those readers skilled in the art.

6. DETAILED DESCRIPTION OF THE INVENTION

Superparamagnetic metal oxides are a unique class of magnetic materials because of their large effects on both the $T_1$ and $T_2$ relaxation times of magnetically active nuclei. We have described in detail the utility of biodegradable superparamagnetic materials as MF contrast agents in related U.S. Pat. Nos. 4,827,945 and 4,770,783, respectively. The disclosures in both Patents are incorporated herein by reference. Others have described the use of superparamagnetic contrast agents since (See, for example, U.S. Pat. No. 4,675,173 issued to Widder; Hemmingson et al. *Acta. Radiologics* 1987, 28(6), 703; Saini et al. *Radiology*, 1987, 162, 211). When present as a component of a superparamagnetic lattice, transition metals, such as iron, are more potent enhancers of proton relaxation than-the same metal as the central ion of a simple paramagnetic chelate. This increased "potency" of the superparamagnetic iron is reflected in, for example, the spin lattice relaxivity value measured for a biodegradable superparamagnetic fluid, comprising the biodegradable superparamagnetic iron oxide and a citrate buffer, which value is 50 times greater than that found for a chelated form of iron. Indeed, as the sizes of the aggregates of iron oxide crystals decrease, their effects on $T_1$ increase relative to their effects on $T_2$. As disclosed in the present invention, superparamagnetic fluids comprised of very small metal oxide aggregates are excellent intravascular MR contrast agents and can be used in a variety of modes including $T_1$-weighted (brightening agents), $T_2$-weighted (darkening agents), or combinations of these and other pulse techniques. The present invention is directed to agents and to a method for the enhancement of MR images of the vascular compartment. The enhancement of the MR image is made possible by the use of a sterile biodegradable superparamagnetic contrast agent whose magnetic component is comprised of three-dimensional aggregate of individual biodegradable superparamagnetic metal oxide crystals.

An important prerequisite for the successful use of biodegradable superparamagnetic materials as intravascular agents in humans is the ability to control the blood lifetimes of the materials. In other words, an effective intravascular agent must have a useful lifetime in the circulatory system so that the MR experiment may be completed before a significant proportion of the administered contrast agent is removed from circulation by organs or tissues of, for example, the reticuloendothelial system (RES). The injection of higher concentrations of any contrast agent will, of course, increase its longevity in the vascular compartment and prolong its effect on the nuclear relaxation times of the blood. Such a strategy, while useful in demonstrating the efficacy of an MR contrast agent in animal models of human pathology, is not ideal for the formulation of a pharmaceutical, clinical form of the contrast agent. Safety considerations preclude the use of overly large doses of a pharmaceutical or diagnostic agent. Imaging techniques, such as those described herein, which are able to enhance the blood pool while maintaining the minimum effective dose are highly desirable. Moreover, the ability of the practitioner to manipulate or control the blood lifetime of the biodegradable superparamagnetic contrast agents of the invention permits an unsurpassed flexibility previously unavailable in the design and operation of the MR experiment. A variety of pharmacokinetic patterns might be used, for example. Hence, for an experiment designed to delineate tissue blood pool volume, an agent with a long blood lifetime would be used having all the advantages outlined above for biodegradable superparamagnetic materials. In other applications, an agent which is rapidly removed from the vascular compartment may be used to "wash in" to damaged tissue and an image taken very soon thereafter. Areas where the blood brain barrier have broken down due to the presence of tumors may be successfully examined using these methods. Moreover, because discrete size ranges of the contrast agent can be obtained, for example, by size exclusion chromatography, the practitioner can tailor and control the amount of tune (e.g., blood halflives) that these agents spend circulating within the vascular compartment. Generally, the blood lifetime is inversely proportional to the overall size of the contrast agent. Some agents of the present invention, because of their extremely small dimensions, are able to circulate within the vascular compartment for relatively long periods of time. In addition the blood half-life of any one of a these agents can also be extended by employing a blocking agent that will compete with the agent for receptors located within the reticuloendothelial system (RES). This technique, as well as its potential applications, are discussed in prior U.S. application Ser. No. 067,586, now U.S. Pat. No. 4,827,945 (Section 6.7, col. 21, line 21-col. 22, line 22). Furthermore, it is the crystalline nature of these agents, which agents characteristically provide solutions of low osmolality compared with paramagnetic agents, in combination with the above-mentioned properties and characteristics makes these biodegradable superparamagnetic metal oxides uniquely suitable as intravascular contrast agents.

The biodegradable superparamagnetic metal oxides can be prepared as a superparamagnetic dispersion or as a superparamagnetic fluid by general methods described previously in applicants' prior co-pending U.S. Patents identified above. These procedures include precipitating the metal oxide crystals, in the presence or absence of a macromolecular or polymeric species, from a solution of the trivalent and divalent ions of a metal by the addition of a sufficient quantity of base. Suitable metal ions include chromium, copper, nickel and tungsten. Preferred metal ions include those of cobalt, iron, manganese, and molybdenum. A solution of hydrated ferric and ferrous salts is particularly preferred. The alkaline reaction may be carried out in the presence of a macromolecular species which aids in dispersing the resultant superparamagnetic metal oxide crystals. In general, the aggregates that form initially, in the absence of the polymeric substance, are larger. The macromolecular species typically has a molecular weight of about 1 to about 250 Kd. Some suitable macromolecular species include polymeric organosilanes, proteins, polypeptides, carbohydrates, mono-, oligo-, or polysaccharides. Preferred macromolecules include human or bovine serum albumin, polyglutamate, polylysine, heparin, hydroxyethyl starch, gelatin, or dextran, with the lattermost being particularly preferred. The dark slurry which forms after the addition of base is then sonicated to further reduce the size of the aggregates. The sonication also serves to oxygenate the mixture and assures the full oxidation of the divalent metal ion to the trivalent oxidation state. Larger particulate aggregates that may form during the procedure may be removed by centrifugation. The resulting supernatant contains only nonparticulate-sized aggregates.

The next stage of the preparation involves the dilution of the supernatant with distilled water and subsequent ultrafiltration through a hollow fiber dialysis apparatus. The diluted supernatant is dialysed against an aqueous solution or buffer of a polyfunctional organic molecule. Molecules containing positively charged groups may be utilized. These molecules may include but are not limited to polylysine, polyornithine, and polyarginine. However, the functional groups of the organic molecule are preferably ionizable to give negatively charged groups such as phosphates, phosphinates, phosphonates, sulfinates, sulfonates, carboxylates, and the like. Polycarboxylate compounds are particularly effective, with salts of citrate ion being most preferred. Besides being commonly used and widely accepted as safe in clinical preparations, the aqueous citrate buffer serves to stabilize the aggregates of the resulting superparamagnetic fluid to further clustering or aggregation. The inventors have found, quite unexpectedly, that the resulting fluid is stable even under the extreme conditions of prolonged heating in an autoclave. In addition, the dialysis step also removes most of the macromolecular species, e.g. dextran. Also, dialysis against citrate scavengers isolated free metal ions probably through coordination with the anionic groups of the polyfunctional molecule. If so desired, greater than ninety percent of the dextran used initially can be removed in this manner. In fact, dextran can make up as little as one percent of the contrast agent.

The resulting dialysed superparamagnetic fluid is then diluted further and sterilized by any means well known in the art. Sterilization may be accomplished by autoclaving, irradiation, sterile filtration, chemical treatment, or other means. Sealing the samples in appropriate containers and heating them in an autoclave is most convenient. It is understood that, depending upon the particular application at hand, substantially all the added macromolecular species may be removed or another introduced by any appropriate means well known in the art including exhaustive dialysis. Typically, weight ratios for the metal oxide to the macromolecular species in the superparamagnetic dispersion or fluid are about 0.01 to about 10 and about 0.01 to about 0.02.

The size distribution and architecture of the metal oxide crystal aggregates can be examined by light scattering methods and by electron microscopy (EM). The EM studies are particularly revealing and show that the aggregates are indeed comprised of individual metal oxide crystals which are interconnected to form irregularly shaped three-dimensional structures (See, for example, FIG. 3). The dimensions of the aggregates depend on the number of component crystals present and, for one specific example, fall in the range of 10–125 nm. The majority of the aggregates have dimensions smaller than about 50 nm. The results of light scattering methods give similar, but slightly larger, values. This slight difference is probably due to the fact that larger particles will tend to scatter more light and thus skew the value slightly toward the higher end. Light scattering methods give a value of about 75 nm for the overall mean diameter of the sample described above.

In a specially modified procedure, extremely small superparamagnetic materials particles are obtained at the outset. In this modification, a solution of ferric and ferrous salts is adjusted first to a pH of about 2.3 before the addition of dextran. The resulting mixture is stirred and heated to about 60°–70° C. for several minutes and then allowed to cool to a temperature of about 40°–45° C. To this solution is added a sufficient amount of ammonium hydroxide to bring the pH to about 10. The resulting suspension is then heated to about 100° C. until a black suspension forms. After an ultrafiltration step to remove most of the unbound dextran, light scattering experiments showed that dextranized particles of this preparation have an overall mean diameter of about 40 nm.

The superparamagnetic fluid prepared according to the general methods can be separated into fractions of decreasing aggregate diameter by size exclusion gel chromatography with a suitable buffer as eluent. The collected fractions are analyzed by UV-vis spectroscopy for metal oxide content and by light scattering methods for an estimate of their crystal aggregate dimensions. Predictably, the larger aggregates elute first followed by the smaller ones. The fractions can be divided into four groups, for the sake of convenience, and tested separately. A standard solution comprised of dextran blue (2,000 kD), ferritin (443 kD), and bovine serum albumin (65 kD) is fractionated under the same conditions as the superparamagnetic fluid. The fraction number or elution volume at which the known proteins emerge serves as points of reference from which the average "molecular weights" of the crystal aggregates of the contrast agent fractions can be related. The results are summarized in Section 7.5.

Proton relaxation experiments are carried out in vivo by intravascularly injecting mice with solutions of fractionated as well as unfractionated contrast agents. The effect on proton relaxation, $T_1$ for example, may be monitored as a function of time for each of the samples, and the results show that the smaller the aggregate size the longer the blood serum lifetime of the contrast agent. The unfractionated superparamagnetic contrast agent shows a moderate serum blood halflife, Blood $t_{\frac{1}{2}}$, of about 13.5 minutes while the smallest aggregates have a Blood $t_{178}$ value of 49.6 minutes.

These superparamagnetic metal oxide preparations serve as excellent contrast agents for MR imaging. They may be successfully used as brightening agents, for example, as can be demonstrated by a relative comparison of the Brightness/Intensity effects of the materials of the invention versus samples of pure water and aqueous solutions of typical paramagnetic $T_1$ relaxation agents such as manganese(II) chloride or ferric chloride. All the superparamagnetic metal oxide preparations described above are able to brighten water signals relative to pure water and in one case, the brightness effects even exceeds that of manganese(II) chloride, heretofore recognized as a very effective $T_1$ contrast agent (See FIG. 4).

7. EXAMPLES

7.1. Preparation of Sterilized Superparamagnetic Fluids

To a vigorously stirred aqueous 16% ammonium hydroxide solution (5 liters) of dextran (2.500 kg, 10–15 kilodalton) is added gradually, and over a 5 minute period, an aqueous solution (5 liters) of ferric chloride hexahydrate ($FeCl_3.6H_2O$, 0.755 kg) and ferrous chloride tetrahydrate ($FeCl_2.4H_2O$, 0.320 kg). The black magnetic slurry which forms is then pumped at a rate of about 0.4 liters per minute through a continuous flow sonicating apparatus. It is sometimes advantageous, although not necessary, to heat the mixture through a sonicating apparatus which comprises a sonicator connected in series to a 100° C. heating coil unit followed by a cooling coil unit. The resulting dispersed mixture is next centrifuged at 2,000×g for 20 minutes to separate the larger aggregates which are discarded.

The supernatant is diluted with deionized, sterile water to a volume of about 20 liters. Ultrafiltration of the diluted supernatant against water and citrate buffer is then carried out in a noncontinuous fashion using a large hollow fiber dialysis/concentrator, Model DC 10 (Amicon Corp., Denvers, Mass.), equipped with a 100 kilodalton molecular weight cutoff dialysis cartridge. In this manner, a substantial amount of the dextran used initially is removed along with any free metal ions.

After ultrafiltration, a solution of 0.20M Fe and 0.025M citrate is obtained by the addition of 1M citrate and adjusting to a pH of about 8 with 1N NAOH. The solution is then autoclaved for 30 minutes (121° C.). Autoclaving is the preferred technique for sterilization since the bottle or container need not be sterile prior to fill. An alternative to sterilization is filtration, but superparamagnetic fluids at high concentrations filter poorly. Dilute superparamagnetic fluids can be filter sterilized, but the added water must then be removed under sterile conditions.

7.2. Further Removal of Dextran from Sterilized Superparamagnetic Fluids

The dextran remaining after ultrafiltration is largely dissociated from the superparamagnetic iron oxide-dextran by autoclaving.

To determine what part of the dextran is attached to superparamagnetic iron oxide after autoclaving, dialysis is used to separate dextran from superparamagnetic iron oxide-dextran complexes. The autoclaved 0.20M Fe solution from above is diluted into 25 mm citrate buffer (pH 8) to an iron concentration of about 2 MM and the solution incubated overnight at 37° C. to release any dextran weakly adsorbed to the superparamagnetic iron oxide. The solution is then applied to a centrifuge micropartition system equipped with a cellulose acetate membrane (Amicon, Denvers, Mass.), where the filtrate is forced through the membrane by centrifugation. The dextran employed initially has a molecular weight of 10–15 kD and passes through the membrane while superparamagnetic iron oxide does not.

Prior to autoclaving (but after ultrafiltration) there were 8.45 mg/ml of dextran present in a solution containing 11.2 mg/ml of Fe (0.2M Fe=11.2 mg Fe/mL). The concentration of dextran passing through the micropartition system membrane was 7.49 mg/mL, indicating that most of the dextran had detached from the superparamagnetic iron oxide by the autoclaving step. Iron is measured by atomic absorption spectrophotometry after dissolving the iron oxide in 0.01N HCl. Dextran is measured by a phenol-sulfuric acid method for total carbohydrates (See, C. E. Meloan and Y. Pomeranz, "Food Analysis Laboratory Experiments," The Avi Publishing Co., Westport Conn., pp. 85–86 (1973)).

The small aggregates of superparamagnetic iron oxide crystals seen in EM studies are largely uncoated after autoclaving and are stabilized through their interactions with polyvalent anions such as citrate. The majority of the dextran is present as a dialyzable species free in solution.

7.3. Modified Procedure for the Preparation of Extremely Small Biodegradable Superparamagnetic Aggregates To an aqueous solution (250 mL) of $FeCl_3.6H_2O$ (35 g) and $FeCl_2.4H_2O$ (16 g) is added a sufficient amount of aqueous 10% sodium carbonate to bring the pH of the solution to a value of about 2.3. Solid dextran (150 g) is then added. The solution is stirred and heated to about 60°–70° C. for about 15 min and then allowed to cool to 40°–45° C. To the reddish solution is added aqueous 7.5% $NH_4OH$ to a final pH between 9.5 and 10.0. A greenish suspension is produced which is subsequently heated to 95°–100° C. for 15 min. The resulting black suspension is then subjected to an ultrafiltration step using an Amicon RA 2000 hollow fiber dialysis-unit equipped with a cartridge having a nominal cutoff of 100 kilodaltons. Light scattering measurements reveal that the dextranized particle has an overall mean diameter of about 40 nm.

7.4. Gel Exclusion Chromatography of Superparamagnetic Materials

Figure 1:
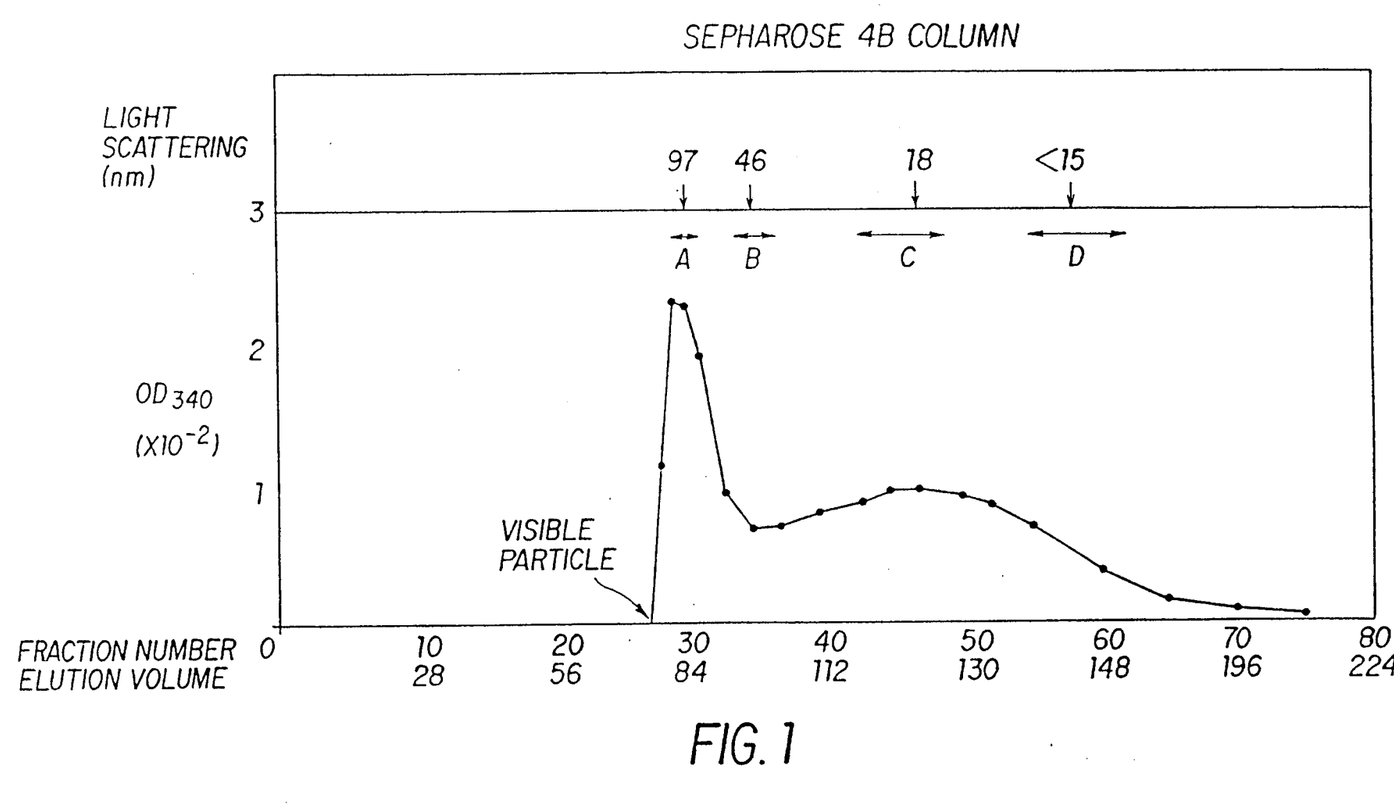
FIG. 1 is a chromatogram obtained from a Sepharose B gel exclusion fractionation of a biodegradable superparamagnetic fluid.

The superparamagnetic fluid described in Section 7.1 can be applied to the top of a chromatography column (2.5 cm×100 cm) packed with Sepbarose 4B. The sample is eluted with 20 mM sodium citrate buffer (pH=8). Fractions are collected and analyzed for their optical density at 340 nm. A separate sample containing a mixture of known proteins is treated and fractionated under the same chromatography conditions. A plot of the optical density (OD) versus the fraction number and elution volume yields a chromatogram which is illustrated in FIG. 1. The overall mean diameter in nanometers may be determined for a given set of superparamagnetic fluid fractions by light scattering methods. These results are listed across the top of FIG. 1. As is readily evident from the chromatogram and plot, the overall size decreases with increasing fraction number and elution time. Likewise, the higher molecular weight proteins elute faster than the smaller ones. The eluted fractions of superparamagnetic materials can be combined as follows: Sample A, fractions 29–31; Sample B, fractions 34–37; Sample C, fractions 43–49; and Sample D, fractions 55–62.

Figure 2:
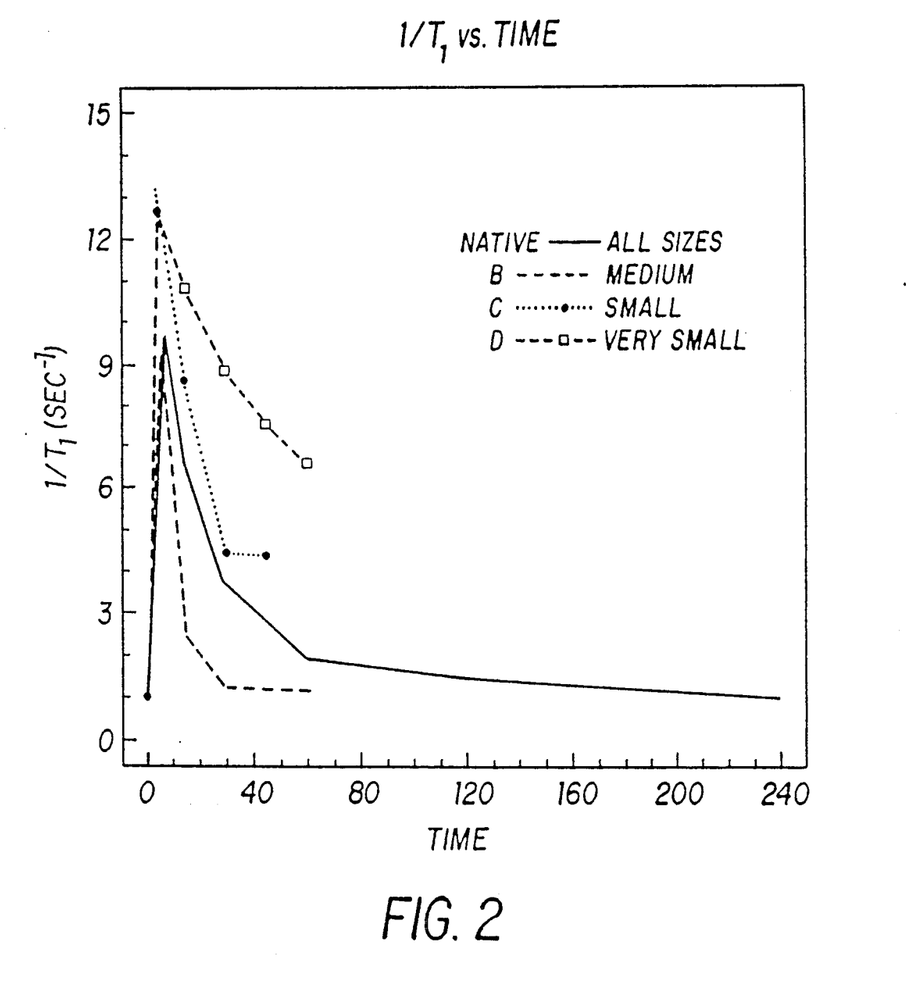
FIG. 2 is a plot of the blood spin-lattice relaxation rate versus time for unfractionated and fractionated superparamagnetic material.

7.5. Determination of Blood Lifetimes of Superparamagnetic Materials as a Function of Size The samples B, C, and D, described above, are intravenously injected separately into a rat at the same dose of 2 mg of iron per kg of rat. The spin-lattice relaxation rate, $1/T_1$, can then be measured as a function of time and reflects the blood concentration. FIG. 2 is a graphical representation of the results for samples B, C, D, and unfractionated superparamagnetic fluid. An examination of the plot in FIG. 2 shows that the blood lifetimes of the different fractions increase with decreasing overall size. Table I summarizes the results of the above experiments. The blood half-life (Blood $t_{\frac{1}{2}}$) is determined from a nonlinear least squares fit to a single exponential decay process. The molecular weight (MW) values of samples A, B, C, and D are those estimated from extrapolated values derived from the standard proteins.

TABLE I

PROPERTIES OF NATIVE AND FRACTIONATED SUPERPARAMAGNETIC FLUID

| Sample | Fraction # | OMD$^a$ | Blood $t_{\frac{1}{2}}$ | Dose |
|---|---|---|---|---|
| Native$^b$ | All | 75 nm | 13.5 min | 1 mg/kg |
| A | 29–31 | 97 | — | 2 |
| B | 34–37 | 46 | 4.05 | 2 |
| C | 43–49 | 18 | 16.6 | 2 |
| D | 55–62 | <15 | 49.6 | 2 |

$^a$Overall mean diameter as measured by light scattering methods.
$^b$Unfractionated fluid prepared by the general methods.

7.6. Transmission Electron Microscopy Studies

Figure 3:
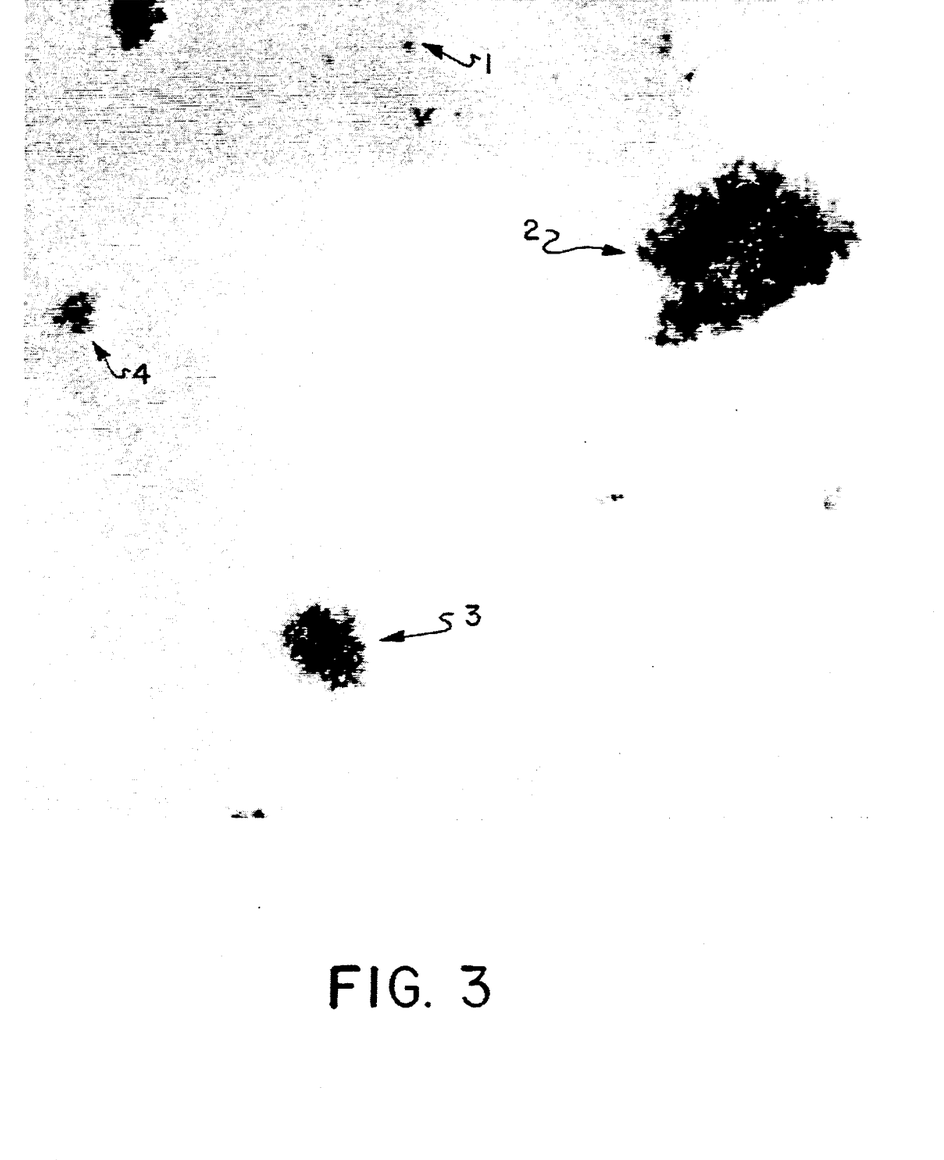
FIG. 3 is an electron micrograph of a sterilized superparamagnetic fluid prepared according to the standard methods of the invention. The metal crystal aggregates numbered 1-5 in the Figure have the following overall mean diameters: 9 nm, 122 nm, 68 nm, and 32 nm, respectively.

An electron micrograph of the sterilized superparamagnetic fluid, prepared according to 7.1 is shown in FIG. 3. The EM study shows the individual particle to be aggregates of iron oxide, with individual iron oxide crystals having a diameter of about 5–7 nm. The crystals of each particle are in direct contact with each other and are not separated by, or embedded in, a matrix or polymer of any kind. EM studies (beyond those shown in FIG. 3) have indicated the presence of aggregates from as small as 10 nm to as large as 400 nm. Both EM and gel chromatography (see Section 7.4) indicate that the superparamagnetic fluid is a heterogeneous mixture of different-sized particles. EM studies reveal the presence of a large number of small aggregates which comprise a very small percentage of the volume of iron mass. Consequently the average volume of an aggregate by EM studies is only about 20 nm. (Average volume = the total volume of all aggregates divided by the total number of aggregates.)

For EM studies it is important to prevent changes in size distribution of particles during sample preparation. The preparation of the sample for EM studies is as follows. A solution of 5% molten agar is added to the sterile superparamagnetic fluid to give a final agar concentration of it and the agar allowed to harden. The agar is minced into pieces of about a millimeter and dehydrated by addition of ethanol/water mixtures of decreasing water content until water is replaced by 100% ethanol. The ethanol is then replaced by propylene oxide in an analogous fashion. The propylene resin finally yielding a 100% epoxy resin which is hardened by curing overnight at 60° C. The hardened resin is then sliced with an ultramicrotone (0.5 micron thick sections) and placed on a 400 mesh copper grid.

A Phillips model 410 LS transmission electron microscope is used to take micrographs at 100 kV.

7.7. Superparamagnetic Fluids as Brightening Agents

Figure 4:
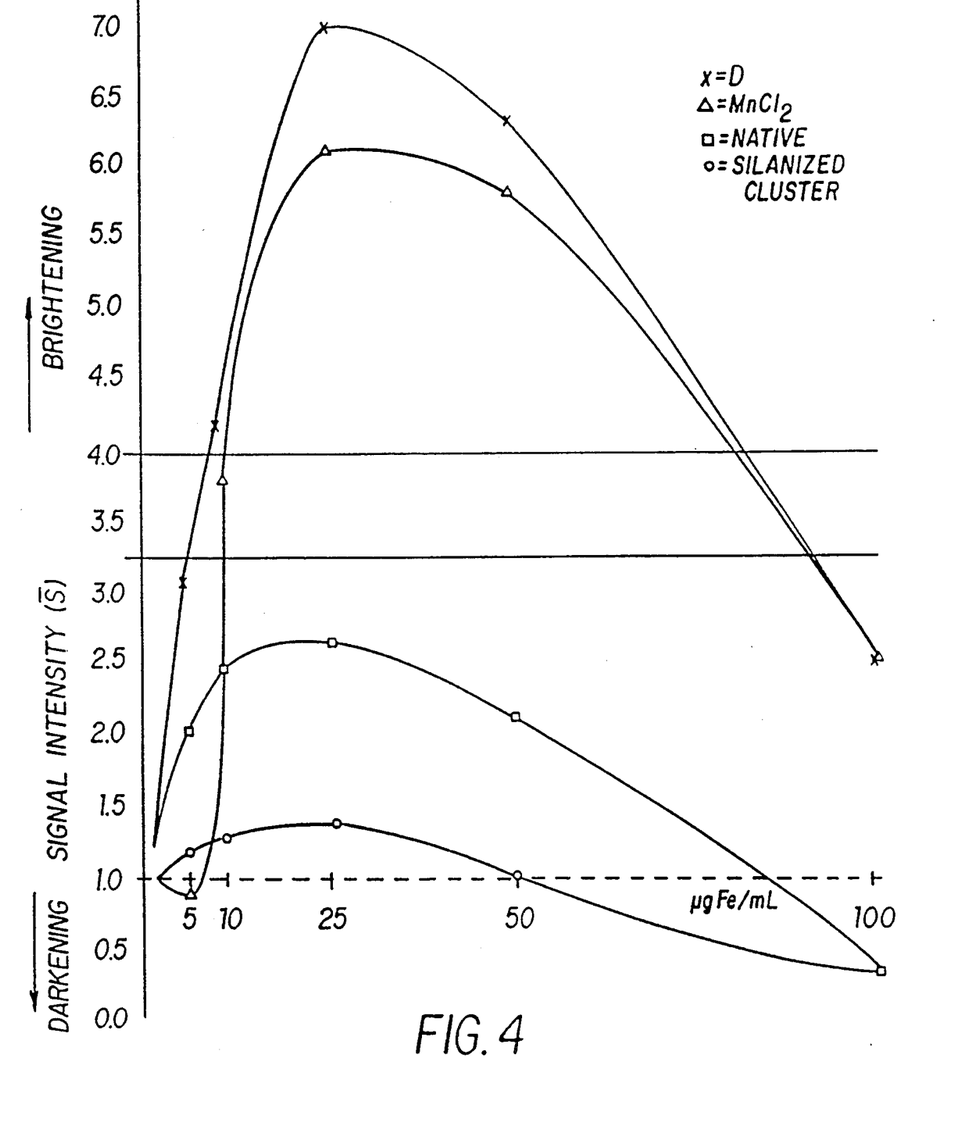
FIG. 4 is a plot of the "brightening" effect of a number of contrast agents as a function of their solution concentration.

Superparamagnetic materials are used as MR contrast agents due to their ability to promote the relaxation of magnetically active nuclei. As the particle size of iron oxide cluster in superparamagnetic fluids becomes smaller and smaller, they become more powerful as brightening agents in $T_1$-weighted MR pulse sequences. FIG. 4 shows the effects of different concentrations of four contrast agents on the signal intensity (S) of an MR image using a $T_1$-weighted pulse sequence of TE=200 msec and TR =15 msec. The imager was a GE CSI 2 Tesla imager. The signal intensity of distilled water is set at 1.0.

Various concentrations of agents were added to distilled water and the molar concentration of metal is given on the x-axis. Agents that brighten increase the value of S while those that darken decrease the value of S. A standard $T_1$ type MR brightening agent is $MnCl_2$ and has a strong image brightening effect over a wide range of concentrations. A standard, more purely $T_2$ type MR agent is provided by a large silanized cluster of superparamagnetic materials made according to the teachings of U.S. Pat. No. 4,695,392 which is incorporated herein by reference. On a molar basis the smallest fraction obtained from the chromatogram of FIG. 1 (D of Table I) is a more potent brightening agent than $MnCl_2$, while the larger parent material (Native of Table I) is considerably less potent as a brightening agent. As shown in FIG. 4, the large silanized cluster is the least potent $T_1$ type agent. The strong effects of sterile superparamagnetic fluids on MR image brightening, particularly as particle size decreases, allows such materials to be used as vascular MR imaging with $T_1$- or $T_2$-weighted pulse sequences. When $T_1$-weighted sequences are used, such materials perform as contrast agents in a manner analogous to paramagnetic brightening agents such as GD/DTPA or $MnCl_2$.

It should be apparent that other modifications and embodiments can be contemplated without departing significantly from the scope and spirit of the present invention. The invention should, therefore, not be limited by the foregoing examples and descriptions thereof but only as enumerated in the following claims.

What is claimed is:

1. A magnetic resonance imaging contrast agent in a physiologically acceptable medium, which contrast agent:
   i) comprises a population of biodegradable superparamagnetic metal oxide particles, wherein said particles (a) are capable of being metabolized or excreted by a subject within about 1 week after administration, as evidenced by a return by proton relaxation rates of an affected organ or tissue of the subject to pre-administration levels; and (b) are associated with a protein; and
   ii) has a blood half-life in the rate of at least about 17 minutes at a dose of about 2 mg of metal per kg of rat.

2. A magnetic resonance imaging contrast agent in a physiologically acceptable medium, which contrast agent:
   (i) comprises a population of biodegradable superparamagnetic metal oxide, wherein said particles (a) are capable of being metabolized or excreted by a subject within about 1 week after administration, as evidenced by a return of proton relaxation rates of an affected organ or tissue of the subject to pre-administration levels, and (b) are associated with a polypeptide; and
   (ii) has a blood half-life in the rate of at least about 17 minutes at a dose of about 2 mg of metal per kg of rat.

3. A magnetic resonance imaging contrast agent in a physiologically acceptable medium, which contrast agent:

(i) comprises a population of biodegradable metal oxide particles, wherein said particles (a) are capable of being metabolized or excreted by a subject within about 1 week after administration, as evidenced by a return of proton relaxation rates of an affected organ or tissue of the subject to pre-administration levels, and (b) are associated with hydroxethyl starch; and (ii) has a blood half-life in the rate of at least about 17 minutes at a dose of about 2 mg of metal per kg of rat.

4. The magnetic resonance imaging contrast agent of claim 1 in which said protein is selected from the group consisting of human serum albumin, bovine serum albumin, gelatin and heparin.

5. The magnetic resonance imaging contrast agent of claim 2 in which said polypeptide is selected from the group consisting of polyglutamate and polylysine.

6. The magnetic resonance imaging contrast agent of claim 1, 2 or 3 in which said particles comprise aggregates of individual biodegradable superparamagnetic metal oxide crystals.

7. The magnetic resonance imaging contrast agent of claim 1, 2 or 3 in which said metal oxide is selected from the group consisting of chromium, cobalt, copper, manganese, molybdenum, nickel and tungsten oxides.

8. The magnetic resonance imaging contrast agent of claim 1, 2 or 3 in which said metal oxide is iron oxide.

9. The magnetic resonance imaging contrast agent of claim 1, 2 or 3 which comprises a population of particles wherein the mean diameter of an individual particle is about 180 Å or less, as measured by light scattering.

10. The magnetic resonance imaging contrast agent of claim 1, 2 or 3 in which said blood half-life is at least about 49 minutes in rat at a dose of 2 mg per metal per kg rat.

11. The magnetic resonance imaging contrast agent of claim 10 in which said protein is selected from the group consisting of human serum albumin, bovine serum albumin, gelatin and heparin.

12. The magnetic resonance imaging contrast agent of claim 10 in which said polypeptide is selected from the group consisting of polyglutamate and polylysine.

13. The magnetic resonance imaging contrast agent of claim 10 in which said particles comprises aggregates of individual biodegradable superparamagnetic metal oxide crystals.

14. The magnetic resonance imaging contrast agent of claim 10 which comprises a population of particles wherein the mean diameter of an individual particle is about 150 Å or less, as measured by light scattering.

15. The magnetic resonance imaging contrast agent of claim 14 in which said polypeptides is selected from the group consisting of polyglutamate and polylysine.

16. The magnetic resonance imaging contrast agent of claim 14 in which said particles comprise aggregates of individual biodegradable superparamagnetic metal oxide crystals.

17. The magnetic resonance contrast imaging contrast agent of claim 14 in which said protein is selected from the group consisting of human serum albumin, bovine serum albumin, gelatin, and heparin.

18. The magnetic resonance imaging contrast agent of claim 1, 2 or 3 in which said macromolecular species has a molecular weight of about 1 to about 250 kd.

19. The magnetic resonance imaging contrast agent of claim 1, 2 or 3 in which said macromolecular species and said metal are present at a weight ratio of about 0.1 to about 10.

20. The magnetic resonance imaging contrast agent of claim 1, 2 or 3 in which said macromolecular species and said metal are present at a weight ratio of about 0.01 to 0.2.

21. The magnetic resonance imaging contrast agent of claim 1, 2 or 3 in which said contrast agent is capable of providing a contrast effect selected from the group consisting of a darkening effect, a brightening effect, and a combined darkening and brightening effect.

22. A method for obtaining an MR image of the vascular compartment of an animal or a human subject which comprises:

(a) administering to such a subject, an effective amount of a magnetic resonance imaging contrast agent in a physiologically acceptable medium, said contrast agent;

(i) comprising a population of biodegradable superparamagnetic metal oxide particles, wherein said particles (a) are capable of being metabolized or excreted by a subject within about 1 week after administration, as evidenced by a return of proton relaxation rates of an affected organ or tissue of the subject to pre-administration levels, and (b) are associated with a protein; and (ii) has a blood half-life in the rat of at least about 17 minutes at a dose of about 2 mg of metal per kg of rat; and (b) recording such MR image of the vascular compartment.

23. A method for obtaining an MR image of the vascular compartment of an animal or a human subject which comprises:

(a) administering to such a subject, an effective amount of a magnetic resonance imaging contrast agent in a physiologically acceptable medium, said contrast agent (i) comprising a population of biodegradable superparamagnetic metal oxide particles, wherein said particles (a) are capable of being metabolized or excreted by a subject within about 1 week after administration, as evidenced by a return of proton relaxation rates of an affected organ or tissue of the subject to pre-administration levels, and (b) are associated with a polypeptide; and (ii) has a blood half-life in the rat of at least about 17 minutes at a dose of about 2 mg metal per kg of rat; and (b) recording such MR image of the vascular compartment.

24. A method for obtaining an MR image of the vascular compartment of an animal or a human subject which comprises:

(a) administering to such a subject, an effective amount of a magnetic resonance imaging contrast agent in a physiologically acceptable medium, said contrast agent (i) comprising a population of biodegradable superparamagnetic metal oxide particles, wherein said particles (a) are capable of being metabolized or excreted by a subject within about 1 week after administration, as evidenced by a return of proton relaxation rates of an affected organ or tissue of the subject to pre-administration levels, and (b) are associated with a hydroxyethyl starch; and (ii) has a blood half-life in the rat of at least about 17 minutes at a dose of about 2 mg metal per kg of rat; and (b) recording such MR image of the vascular compartment.

25. The method of claim 22 in which said protein is selected from the group consisting of human serum albumin, bovine serum albumin, gelatin and heparin.

26. The method of claim 21 in which said polypeptide is selected from the group consisting of polyglutamate and polylysine.

27. The method of claim 22, 23 or 24 in which said particles comprise aggregates of individual biodegradable superparamagnetic metal oxide crystals.

28. The method of claim 22, 23 or 24 in which said metal oxide is selected from the group consisting of chromium, cobalt, copper, manganese, molybdenum, nickel and tungsten oxides.

29. The method of claim 22, 23 or 24 in which said metal oxide is iron oxide.

30. The method of claim 22, 23 or 24 which comprises a population of particles wherein the mean diameter of an individual particle is about 180 Å or less, as measured by light scattering.

31. The method of claim 22, 23 or 24 in which said blood half-life is at least about 49 minutes in rat at a dose of 2 mg per metal per kg rat.

32. The method of claim 22, 23 or 24 in which comprises a population of particles wherein the mean diameter of an individual particle is about 150 Å or less, as measured by light scattering.

33. The method of claim 22, 23 or 24 in which said macromolecular species has a molecular weight of about 1 to 250 kd.

34. The method of claim 22, 23 or 24 in which said macromolecular species and said metal are present at a weight ratio of about 0.01 to about 10.

35. The method of claim 22, 23 or 24 in which said macromolecular species and said metal are present at a weight ratio of about 0.01 to about 0.2

36. The method of claim 22, 23 or 24 in which said contrast agent is capable of providing a contrast effect selected from the group consisting of a darkening effect, a brightening effect, and a combined darkening and brightening effect.

37. The method of claim 31 in which said protein is selected from the group consisting of human serum albumin, bovine serum albumin, gelatin and heparin.

38. The method of claim 31 in which said polypeptide is selected from the group consisting of polyglutamate and polylysine.

39. The method of claim 31 in which said particles comprise aggregates of individual biodegradable superparamagnetic metal oxide crystals.

40. The method of claim 32 in which said protein is selected from the group consisting of human serum albumin, bovine serum albumin, gelatin and heparin.

41. The method of claim 32 in which said polypeptide is selected from the group consisting of polyglutamate and polylysine.

42. The method of claim 32 in which said particles comprise aggregates of individual biodegradable superparamagnetic metal oxide crystals.

* * * * *

UNITED STATES PATENT AND TRADEMARK OFFICE
CERTIFICATE OF CORRECTION

PATENT NO. : 5,314,679

DATED : May 24, 1994

INVENTOR(S) : Lewis et al.

It is certified that error appears in the above-identified patent and that said Letters Patent is hereby corrected as shown below:

In col. 3, lines 2-3, replace "ad actions" with --adverse reactions--

In col. 3, line 21, replace "YR" with --MR--

In col. 5, line 25, replace "MF" with --MR--

In col. 5, line 35, replace "than-the" with --than the--

In col. 5, line 48, replace "$T_1 i$-weighted" with --$T_1$-weighted--

In col. 5, line 68, replace "cf" with --of--

In col. 6, line 31, replace "tune" with --time--

In col. 8, line 12, delete "materials"

In col. 8, line 56, replace "Blood $t_{178}$" with --blood $t_{1/2}$--

In col. 11, line 24, insert --Section-- before "7.1"

In claim 1, col. 12, line 48, replace "rate" with --rat--

In claim 2, col. 12, line 63, replace "rate" with --rat--

In claim 3, col. 13, line 9, replace "rate" with --rat--

In claim 17, col. 13, line 60, delete the first "contrast"

UNITED STATES PATENT AND TRADEMARK OFFICE
CERTIFICATE OF CORRECTION

PATENT NO. : 5,314,679
DATED : May 24, 1994
INVENTOR(S) : Lewis et al.

It is certified that error appears in the above-indentified patent and that said Letters Patent is hereby corrected as shown below:

In claim 31, col. 15, line 28, replace "in rat" with --in the rat--

Signed and Sealed this

Seventeenth Day of September, 1996

Attest:

BRUCE LEHMAN

Attesting Officer        Commissioner of Patents and Trademarks